United States Patent [19]
Ritchey

[11] 3,948,632
[45] Apr. 6, 1976

[54] CONTROL OF ALGAE, AQUATIC PLANTS, AND THE LIKE

[76] Inventor: Edward R. Ritchey, 303 S. Fifth St., St. Joseph, Mo. 64501

[22] Filed: Apr. 8, 1974

[21] Appl. No.: 458,989

[52] U.S. Cl. .............................. 71/88; 71/66; 71/67
[51] Int. Cl.² ........................................... A01N 9/28
[58] Field of Search ........................... 71/66, 67, 81

[56] References Cited
UNITED STATES PATENTS

| | | | |
|---|---|---|---|
| 2,576,083 | 11/1951 | Tischler | 71/81 X |
| 2,637,641 | 5/1953 | Tischler | 71/81 X |
| 3,761,238 | 9/1973 | Errede | 71/66 X |

Primary Examiner—Lewis Gotts
Assistant Examiner—Catherine L. Mills
Attorney, Agent, or Firm—John H. Widdowson

[57] ABSTRACT

An algaecide-herbicide composition of matter and process for applying same. The matter comprises a major proportion of a first compound having an alkanolamine and a copper salt selected from the group consisting of copper sulfate, copper chloride, copper acetate, copper nitrate, and mixtures thereof, and a minor proportion of a second compound having the formula

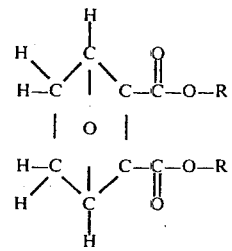

wherein R is selected from the group consisting of sodium, potassium, and mixtures thereof.

5 Claims, No Drawings

CONTROL OF ALGAE, AQUATIC PLANTS, AND THE LIKE

BACKGROUND OF THE INVENTION

1. Field of the Invention

This invention is related to an algaecide-herbicide composition of matter. More specifically, this invention provides a chemical mixture and process for applying same for controlling the growth of algae, aquatic plants, and the like, in ponds, lakes, and other bodies of water.

2. Description of the Prior Art

There are many chemical mixtures and agents which kill or inhibit algae and aquatic weed growth, but each of these chemical mixtures or agents is plagued with at least one disadvantage which hinders its usage. Copper sulfate has been numerously utilized as an algaecide for killing and controlling the growth of algae in waters having a pH below 7. In waters having bicarbonates, carbonates and/or a pH over 7, it has long been known that copper sulfate is most ineffective because of copper precipitating in the form of copper hydroxide or copper carbonate. Copper ions are primarily responsible for the killing action of copper sulfate, and without these toxic copper ions, copper sulfate is essentially harmless to algae and the like. Copper alkanolamine salts have been used for maintaining toxic copper ions in solution for effectively killing algae but water treated with these alkanolamine salts cannot be used for swimming within 24 hours after treatment. Water treated with copper alkanolamine salts also cannot be used for irrigation, agricultural sprays, food crops or other domestic purposes within 7 days of treatment. Disodium and dipotassium salts of endothall (e.g. 3,6-endoxohexahydrophthalic acid) have been used for aquatic weed killing or inhibiting, and have been more effective than copper sulfate. However, these salts are very slow in their action and fish from treated waters cannot be used for food or feed within 3 days after treatment.

SUMMARY OF THE INVENTION

It is therefore an object of this invention to provide an algaecide-herbicide composition of matter and process for applying same which does not contain the deficiencies associated with the prior art.

It is another object of this invention to provide a novel algaecide-herbicide mixture and process for applying same which is safe, effective, and has adequate lasting effect in the elimination of algae and sundry aquatic plants.

It is yet another object of this invention to provide an algaecide-herbicide composition of matter and process for applying same which when applied to water provides within 24 hours a safe and usable body of water for recreation, human consumption, and one which is without harm to fish.

It is still yet another object of this invention to provide an algaecide-herbicide composition of matter and process for applying same which does not have any heavy latent residue of harmful chemicals and is relatively economical to manufacture.

Still other objects will be apparent to those skilled in the art from the following description of this invention.

The foregoing objects are achieved by the practice of this invention. Broadly, this invention accomplishes its desired objects by providing an algaecide-herbicide composition of matter comprising a major proportion of a first compound having an alkanolamine and a copper salt selected from the group consisting of copper sulfate, copper chloride, copper acetate, copper nitrate, and mixtures thereof, and a minor proportion of a second compound having the formula

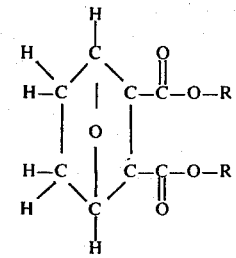

wherein R is selected from the group consisting of sodium, potassium, and mixtures thereof. The process for killing algae, aquatic weeds, and the like, in ponds, lakes, and other bodies of water comprises contacting the algae and aquatic weeds with the novel algaecide-herbicide composition of matter at a rate of between about 1/6 gallon to about 6.5 gallons per each 1 acre-foot of water in the ponds and lakes. The mixture is preferably admixed before applying with between about ½ to about 6 parts of water per 1 part of mixture.

Thus, by the practice of this invention, there is provided an economical, novel process for applying a synergistic, new algaecide-herbicide composition of matter to algae, aquatic weeds, and the like, (for killing and inhibiting the same) in ponds, lakes, and other bodies of water.

DETAILED DESCRIPTION OF THE INVENTION

The novel algaecide-herbicide synergistic composition of matter of my invention is brought into contact with algae, aquatic weeds, and the like, in ponds, lakes, and other bodies of water. It may be applied at any suitable rate but is preferably applied at a rate of between about 1/6 gallon to about 6.5 gallons per each 1 acre-foot of water in the lakes or ponds; more preferably, it is applied at a rate of between about ⅓ gallon to about 3.25 gallons; and most preferably at a rate of about ⅔ of a gallon per 1 acre-foot of water. A working solution of my new algaecide-herbicide chemical mixture is prepared by preferably admixing before applying with any suitable amount of water, which in a preferred embodiment is between about ½ to about 6 parts of water per 1 part mixture; and in a more preferred embodiment is between about 1 to about 3 parts of water per 1 part of the mixture. The latter more peferred admixing proportion is equivalent to a concentration range of from between about 0.5 p.p.m. to about 5.0 p.p.m.

My new, synergistic algaecide-herbicide chemical mixture comprises a major proportion of a compound including an alkanolamine (or an ester or the salt of an alkanolamine) and a copper salt, and a minor proportion of a compound (hereinafter referred to as the "second compound") having the formula

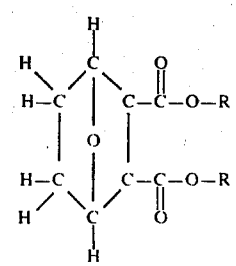

wherein R is selected from the group consisting of sodium, potassium, and mixtures thereof. Preferably, R is potassium.

The alkanolamine may be selected from the group consisting of dimethylethanolamine, diethylethanolamine, aminoethylethanolamine, monoethanolamine, diethanolamine, triethanolamine, monoisopropanolamine, diisopropanolamine, triisopropanolamine, methyldiethanolamine, and mixtures thereof. In the preferred embodiment of the invention, the alkanolamine is triethanolamine because of economics and the effect it has on the copper salt in maintaining the toxic copper ions in solution.

The copper salt which is combined with the alkanolamine may be any suitable copper salt but is preferably one selected from the group consisting of copper sulfate, copper chloride, copper acetate, copper nitrate, and mixtures thereof. More preferably, the copper salt is copper sulfate because it is inexpensive and is available.

It has been discovered that the alkanolamine may be combined with the copper salt in any suitable amount, but in the preferred embodiment comprises from between about 50% wt. to about 65% wt. of the combination of copper salt and alkanolamine. This is an equivalent of from about 1 to about 2 parts by weight of alkanolamine per 1 part by weight of the copper salt. This is also equivalent to about 7.0% wt. of elemental copper (or an alkanolamine/copper salt compound having a concentration of about 0.76 lbs. of copper per gallon), and about 93.0% wt. of the alkanolamine. These proportions enable better attainment of the (toxic) copper ions in solution when alkaline waters having carbonates and alkaline earth metals are utilized.

The alkanolamine/copper salt compound may be combined with the second compound in any suitable quantity but preferably comprises from between about 35% wt. to about 65% wt. of the algaecide-herbicide chemical composition. My synergistic chemical composition has been found to be more economical if it is diluted with water before utilizing it as a working solution. The diluting should be such as to have my algaecide-herbicide solution comprising water, from between about 35% to about 65% wt. of the alkanolamine/copper sulfate compound, and from about 23% wt. to about 43% wt. of the second compound. The more preferred embodiment of the invention comprises water, from between about 25% wt. to about 41% wt. of the second compound, and from between about 45% to about 55% wt. of the alkanolamine/copper salt compound. The most preferred embodiment of the invention comprises about 17% wt. water, about 50% wt. of the second compound, and about 33% wt. of the alkanolamine/copper salt compound. As aforementioned, my new synergistic algaecide-herbicide chemical solution is preferably prepared as a working solution by admixing with water before applying it to the aquatic weeds and algae.

In the following is set forth examples of my novel, synergistic algaecide-herbicide composition of matter and process for applying same which are given by way of illustration and not by limitation. The remarkable synergistic effect of my invention will be illustrated in the examples. The specific concentrations, percent killing or inhibiting, compounds, times, and various other parameters set forth in these examples are not to be construed to unduly limit the scope of the invention.

EXAMPLE I

My synergistic algaecide-herbicide composition of matter comprising 17% wt. water, 33% wt. of the second compound having R as potassium, 50% wt. of the triethanolamine/copper sulfate compound mixed in a proportion of about 2 parts of triethanolamine per 1 part of copper sulfate, was prepared in a working solution by admixing 1 part of my algaecide-herbicide chemical solution with about 3 parts water. Separate solutions of copper sulfate, the second compound having R as potassium, and a 2 to 1 mixture of triethanolamine and copper sulfate, respectively, were also prepared.

Tests are conducted in a 32 acre-foot fresh water pond containing Cladophera, Elodea, and Sago pond weed, Tribonerma, Pithophora and Spirogyra. The 32 acre-foot pond is divided into four 8 acre-foot sections and each of the four previously mentioned solutions is applied at a rate of about ⅔ of a gallon per 1 acre-foot of water in the pond which is equivalent to about 0.05 p.p.m. The following two tables indicate the results after 24 hours:

TABLE I

| Chemical Agent | % Control | | |
|---|---|---|---|
| | Cladophera | Elodea | Sago |
| 1. My synergistic algaecide-herbicide composition of matter | 100 | 100 | 100 |
| 2. CuSO$_4$ | 8 | 5 | 7 |
| 3. The 2:1 mixture of triethanolamine and CuSO$_4$ | 15 | 20 | 18 |
| 4. The second compound having R as Potassium | 30 | 25 | 35 |

TABLE II

| | | Pithophora | Spirogyra | Tribonerma |
|---|---|---|---|---|
| 1. | Same as above | 100 | 100 | 100 |
| 2. | " | 16 | 10 | 14 |
| 3. | " | 20 | 23 | 30 |
| 4. | " | 26 | 30 | 28 |

EXAMPLE II

The same chemical solutions of EXAMPLE I are utilized in testing their control on a 20-acre plot of crabgrass and lambsquarter. Upon completion of the test, the following data are observed:

TABLE III

| | Chemical Agent | Rate lbs./acre | % Control | |
|---|---|---|---|---|
| | | | Crabgrass | Lambsquarter |
| 1. | Same as hereinbefore | .5 | 100 | 100 |
| 2. | " | 3.0 | 15 | 10 |
| 3. | " | 1.3 | 45 | 48 |
| 4. | " | 1.5 | 44 | 40 |

EXAMPLE III

Following the details of EXAMPLE I and varying in my algaecide-herbicide composition of matter the triethanolamine, the R, the copper salt, and the mixing proportions of all compounds, it can be observed (when all results are obtained) that my algaecide-herbicide composition of matter is similarly effective and controls the aforementioned algae and herbs better than the other three chemical solutions. These results are observed after over 25 tests are run.

The foregoing examples illustrate that neither copper sulfate, nor the 2:1 mixture of triethanolamine and copper sulfate, nor the dipotassium salt of endothall (i.e. the second compound having R as potassium) are as effective as my novel synergistic algaecide-herbicide composition of matter in controlling Cladophera, Elodea, Sago pond weed, Tribonerma, Pithophora, Spirogyra, Crabgrass, or Lambsquarter. It can be readily observed that upon combining these three chemical solutions in various previously mentioned mixing proportions to comprise my new chemical solution, unexpected additive results are observed yielding a synergistic mixture.

The alkanolamine/copper salt compound may be mixed with the second compound before treating the algae and/or herbs in the water, and processed either into a solid phase by desiccating, or into a concentrated aqueous solution. The alkanolamine, the copper salt, and the second compound, as an alternative, may each be introduced separately into the water. The former is the most preferred means of treating the algae and herbs. If the latter process is utilized, the alkanolamine should be added into the water prior to (or simultaneous with) the copper salt in order to maintain the toxic copper ions in solution. The second compound may be added prior or after or simultaneous with the introduction of the alkanolamine.

While the present invention has been described herein with reference to particular embodiments thereof, and specific examples, a latitude of modification, various changes and substitutions are intended in the foregoing disclosure, and in some instances some features of the invention will be employed without a corresponding use of other features without departing from the scope of the invention as set forth.

I claim:

1. A process for killing terrestrial plants, which comprises contacting said plants with a mixture comprising about 17% wt. water, about 33% wt. of a compound having the formula

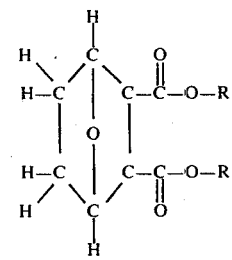

wherein R is potassium, and about 50% wt. of a triethanolamine/copper sulfate compound mixed in a proportion of about 2 parts of triethanolamine per 1 part of copper sulfate.

2. The process of claim 1 additionally including admixing said mixture with about 3 parts of water per 1 part of said mixture.

3. The process of claim 2 wherein said triethanolamine/copper sulfate compound comprises about 0.76 lbs of copper per gallon.

4. The process of claim 3 additionally including applying said admixed mixture at a rate of between about ⅓ gallon to about 3.25 gallons per each 1 acre-foot.

5. The process of claim 1 wherein said copper sulfate compound comprises about 7.0% wt. of elemental copper.

* * * * *